United States Patent [19]

Lipp

[11] 4,231,371
[45] Nov. 4, 1980

[54] ELECTRICALLY HEATED SURGICAL CUTTING INSTRUMENT

[75] Inventor: George D. Lipp, Painted Post, N.Y.

[73] Assignee: Corning Glass Works, Corning, N.Y.

[21] Appl. No.: 961,191

[22] Filed: Nov. 16, 1978

[51] Int. Cl.³ .............................................. A61B 17/38
[52] U.S. Cl. ................................. 128/303.1; 30/140; 219/233; 219/241
[58] Field of Search ........... 128/303.1, 303.13, 303.14, 128/303.17, 303.18; 30/140; 219/240, 241, 233, 227–229

[56] References Cited

U.S. PATENT DOCUMENTS

| | | | |
|---|---|---|---|
| 3,286,077 | 11/1966 | Redford et al. | 219/241 X |
| 3,634,652 | 1/1972 | Shimizu et al. | 128/303.18 X |
| 3,826,263 | 7/1974 | Cage et al. | 128/303.1 |
| 3,933,157 | 1/1976 | Bjurwill | 128/303.14 |
| 4,074,719 | 2/1978 | Semm | 128/303.1 |
| 4,089,336 | 5/1978 | Cage et al. | 128/303.1 |

FOREIGN PATENT DOCUMENTS

1139927  11/1962  Fed. Rep. of Germany ...... 128/303.13

Primary Examiner—Lee S. Cohen
Attorney, Agent, or Firm—John P. DeLuca; Burton R. Turner

[57] ABSTRACT

A surgical cutting instrument includes an electrically heated cutting edge and a power supply system for maintaining the cutting edge at a constant high temperature for sterilizing the blade, cutting tissue and cauterizing the incised tissue to reduce hemorrhage from the cut surfaces of the tissues (hemostasis).

6 Claims, 2 Drawing Figures

ELECTRICALLY HEATED SURGICAL CUTTING INSTRUMENT

BACKGROUND OF THE INVENTION

The control of bleeding during surgery accounts for a major proportion of the total time involved in an operation. The bleeding that occurs when tissue is incised obscures the surgeon's vision, reduces his precision and often dictates slow and elaborate procedures in surgical operation. Each bleeding vessel must be grasped in pincer like clamps to stop the flow of blood and the tissue and vessel within each clamp must then be tied with pieces of fine thread. These ligated masses of tissue die and decompose and thus tend to retard healing and promote infection.

The invention described herein is a hemostatic surgical cutting instrument incorporating an electrically heated edge, where it is desirable to minimize a number of external electrical connections to a series of electrical elements.

Accordingly, the present invention provides a surgical cutting instrument having a heating element which is electrically heated to a constant high temperature for sterilizing the blade, and cauterizing the surfaces of the incision, thereby allowing surgery to be more rapidly performed. It is accomplished in accordance with the illustrated embodiment of this invention by providing an electrically heated element adjacent the cutting edges of the blade and by providing a control system which maintains the cutting edge at a high substantially constant temperature during its use.

The temperature at which the cutting edge of the blade is maintained depends upon such factors as the nature of the tissue to be cut, the speed of the cutting desired, the degree of tissue coagulation desired and the nonadherence of the blade to the incised tissue and generally is maintained between 200°-300° C. for typical incisions. The handle of the cutting instrument is thermally insulated from the blade to permit comfortable use of the instrument and the handle and blade with its electrically heated cutting edge are detachable for easy replacement and interchangeability.

SUMMARY OF THE INVENTION

According to the present invention the instantaneous temperature of the cutting edge is monitored by measuring the resistance of the heating element or elements and the monitoring signal thus derived provides an inferred value for temperature which may be used to control the power applied to portions or segments of the heating element.

DESCRIPTION OF THE PREFERRED EMBODIMENT

Figure 1:
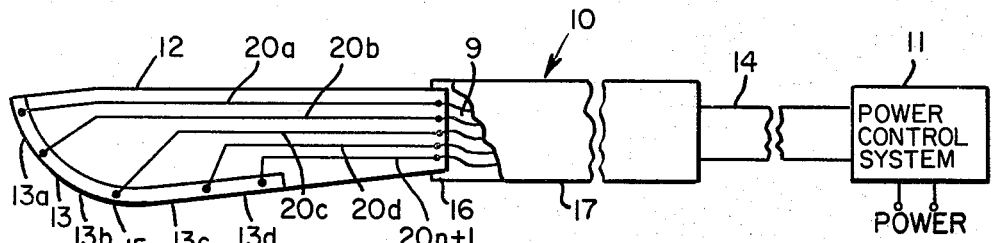
FIG. 1 is a schematic diagram showing a hemostatic cutting instrument according to a preferred embodiment of the present invention.

Referring now to FIG. 1 of the drawing there is shown one side of surgical cutting instrument 10 connected to a temperature measuring and power controlling system 11. The cutting instrument 10 includes a thin glass, glass-ceramic, or ceramic card which may be hereinafter referred to as a substrate or blade 12 in the desired shape of a surgical cutting blade which is detachable from handle or holder 17. An electrically energized heating element 13 is disposed along leading edge 15 of the blade 12 hereinafter referred to as the cutting edge 15. The heating element 13 is connected to the control circuit 11 via a cable 14, having a selected number of conductors 9, and connector 16 in handle 17.

The heating element 13 may be a single filament attached to the edge of the blade 12, for example a layer of electrically conductive material, vapor deposited along the cutting edge 15 of blade 12 such as tin oxide. In a preferred embodiment the material used in heating element 13 should have a negative temperature coefficient of resistance, so that, as selected portions of the element cool when in contact with tissue, the resistance of such portions will increase and thereby provide an indication of those portions of the heating element 13 in which additional power should be supplied by the control system 11. The temperature of the heating element 12 may thus be maintained substantially constant along the entire length thereof as portions thereof contact tissue. Suitable materials having a negative temperature coefficient of resistance include silicon carbide, carbon, boron silicate, and such semiconductor materials as silicon and germanium and also antimony doped tin oxides. Of course, materials having a positive coefficient of resistance may also be used as an element providing indication of temperature.

For general cutting applications, the heating element 13 may consist of a plurality of electrically isolated elements or segments 13a–13d, as shown in FIG. 1, with each of the elements 13a–13d connected to a separate temperature measuring and power controlling portion of the control system 11. For purposes of explanation of FIG. 1 only four segments 13a–13d are illustrated, but more may be provided within the limits of space on substrate 12. In a preferred embodiment the substrate 12 carries eight segments on each side of the blade 12. The back side not shown is a mirror image of the profile illustrated.

Figure 2:
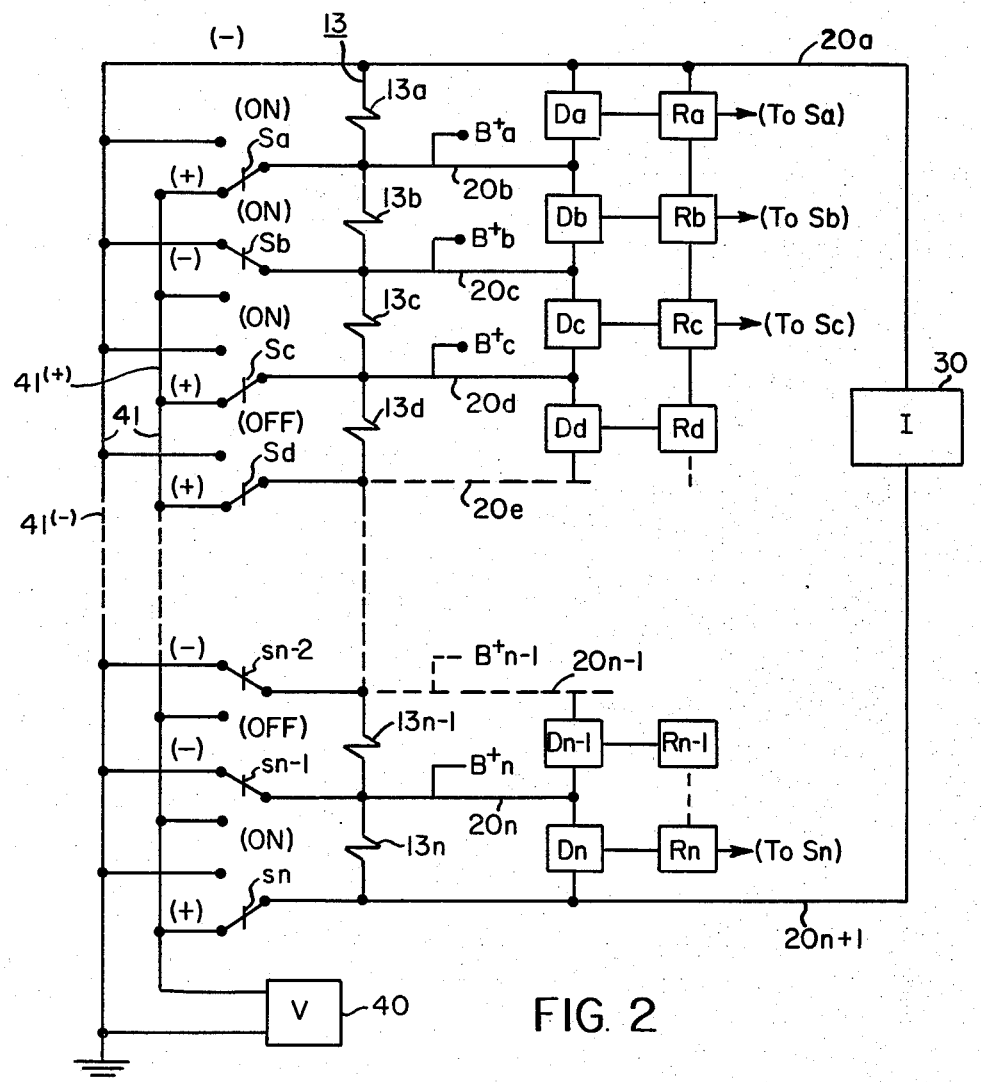
FIG. 2 is a diagram illustrating schematically the control concept of the present invention with an equivalent circuit for the heating element shown.

In FIG. 2 the circuit illustrates a system having n segments hereinafter described. In the illustrative example of FIG. 1, the heating element 13 of hemostatic surgical cutting instrument 10 is formed as a continuous electrically conducting film deposited on each side of the cutting edge 12 with portions of the heating element 13 electrically segmented from other portions as illustrated by reference numerals 13a–13d. For each segment beginning with 13a for example, a pair of leads 20a and 20b are deposited or printed on the body of the substrate 12 and may be adapted to be coupled with the cable 14 by connectors 16. The leads 20a and 20b form a portion of the power circuit for the segment 13a. Similarly leads 20b and 20c form portions of a circuit for the segment 13b and likewise down through connectors 20d and 20n+1 for segment 13d. Leads 20a and 20n+1 are coupled to the extreme ends of the heating element 13 as illustrated and may act as test leads in addition to the power carrying function. As test leads, the conductors 20a and 20n+1 are provided with an input from the control system 11 for delivering a test current to the heating element 13, which will assist in the measurement of the various resistances (and thus inference of temperature) of the various segments 13a–13d.

It should be understood that the surgical cutting instrument 10 of the present invention is a rather small device and the space requirements on the substrate 12 severely restrict the circuitry which may be printed or deposited thereon. Thus the present invention provides for a means by which the number of leads printed on the substrate 12 may be reduced without a sacrifice of available control for each of the segments 13a through 13d. Furthermore the control system 11 of the present invention is adapted to control each of the segments 13a–13d independently of the other segments by allowing the electrical potential across any one segment 13a through 13d to float between selected values which is sufficient to maintain that segment at the desired temperature. Other sections adjacent thereto may be maintained at the same or different floating potentials independent of the one just described and thus each segment may be independently controlled with a minimum number of electrical connections thereto.

The control system 11 may be of the type described in copending application of D. Johnson, Ser. No. 961,188 filed this same date and assigned to Corning Glass Works, the assignee herein.

In FIG. 2 the control concept of the present invention is detailed. An equivalent circuit of n series resistors 13a–13n represents the heating element 13 and each is referenced the same as each segment 13a–13n in FIG. 1. Leads 20a through 20n+1 carry test current from a current source 30 and heating power from a voltage source 40.

Constant current source 30 imposes a test current on heating element 13. Each element 13a through 13n has associated therewith a respective detector Da–Dn coupled over a pair of leads 20a–20b; 20b–20c . . . 20n–20n+1. Detectors Da–Dn measure the voltage drop which is proportional to the resistance of the segment and produce control output. Relays Ra–Rn are respectively coupled to corresponding detectors Da–Dn and respond to the control output thereof. Relays Ra–Rn control respective switches Sa–Sn. Each relay Ra–Rn is responsive to a reference signal which determines the polarity of its response hereinafter explained.

The segment 13a represents one portion of the blade heating element 13 which may be operating at a selected temperature in accordance with whether or not it is in contact with incised tissue. If the segment 13a is in contact with tissue it will cool and its resistance will increase. The increase in resistance is sensed by detector Da and an output thereof controls relay Ra which moves switch Sa to a (positive) terminal 41 (+) on power bus 41 coupled across leads 20a–20n+1. Thus voltage source 40 provides power to segment 13a from the positive side of bus 41 through switch Sa, segment 13a lead 20a to the negative side of bus 41 to ground. In the case of segment 13a the reference signal is a ground potential (negative side 41 (—) of bus 41) applied to lead 20a. If the segment 13a is at or above the temperature limit the detector Da would not call for power thus relay Ra would switch to the negative (—) side of bus 41 leaving the segment 13a off since both sides would be coupled to ground potential.

In FIG. 2 each segment 13a–13n is in a selected conduction state (ON) or (OFF) for purposes of illustration. Each may be switched to a different state as hereinafter described. It will be assumed that the segment 13b has cooled such that detector Db calls for power to be applied to the segment 13b and thus activates relay Rb controlling switch Sb to the position shown. In this situation however the switch Sb is contacted with the negative side of the bus 41 thus power is delivered from the voltage source 40 over the negative side thereof 41 (—) to switch Sb through the segment 13b and thereafter through the switch Sa to the positive side 41 (+) of the bus 41 back to the voltage source 40. It should be realized that the relay Rb is not only responsive to detector Db but also to the condition of a reference signal which indicates the condition of at least one side of the heating segment 13b, namely the side of the element 13b coupled to the switch Sa. Since this condition is a function of the condition of the previous relay Ra, the relay Rb is responsive to the condition of relay Ra. Segment 13c is coupled across bus 41 from the top of the drawing in a (—) to (+) polarity. Thus relay Rb requires that its switch Sb complete a power circuit across bus 41 in a (+) to (—) polarity if power is to be delivered to segment 13b.

Similarly in FIG. 2 the section or segment 13c also requires power. In this situation the relay Rc responds to the condition of the relay Rb. Since upper side of the segment 13c (conductor 20c) is already coupled to the negative side 41 (—) of bus 41 through the switch Sb, relay Rc activates switch Sc to couple the lower conductor 20d to the positive side 41 (+) of the bus 41.

The segment 13d for the particular example herein requires no power (OFF) during the interval under discussion. Thus the relay Rd sensing the condition of its upper conductor 20d by the condition of relay Rc, couples the conductor 20e via switch Sd to the positive side 41 (+) of the bus 41 so that the segment 13d is shunted out of the power circuit. This sequence continues over the entire length of heater element 13. Thus in the example discussed herein segment 13 n—1 is in an (off) condition but in this case its terminals 20n—1 and 20n are both coupled to the negative side 41 (—) of bus 41. In segment 13n the relay Rn couples switch Sn to the positive side 41 (+) of the bus 41 to provide power to that segment. The reference signal herein is essentially the potential of one side of the segment as determined by the condition of the connection between the adjacent segments. This control could be actuated by observation. However, in the preferred embodiment detectors Da and relays Ra may be electronic controls as described in the aforementioned patent application of D. Johnson.

The power portion of the circuit of FIG. 2 including the voltage source 40 and bus connection 41 through switch Sa–Sm to segments 13a–13n is independent of the sensing portion of the circuit described above. The current source 30 which provides power to measure the voltage drop of each segment 13a–13n may be DC while the voltage source 40 may be AC or vice versa. The voltage source 30 and current source 40 may be time separated in operation as in Johnson noted above so that the power function does not overwhelm the detection function.

An important feature of the present invention is that, it reduces the number of leads which are required to control the various segments 13a to 13n of the heating element 13 while at the same time providing individual control to each of said segments.

For more individualized control each of the segments 13a–13n may be biased to a particular respective potential Ba–Bn as indicated in the drawing of FIG. 2. For example the lead 20b has imposed thereon a potential Ba and similarly the lead 20c has potential Bb and so forth. The potentials 13a–13n may be positive, negative or neutral depending upon the calibration of the particular segment required. If desired, it is possible to bias the segments 13a to 13n notwithstanding the requirement for power.

Appropriate logic circuits may be utilized to control switches described. For example in the D. Johnson application referred herein, exclusive OR circuits are utilized to establish the polarity of the individual segments in accordance with the polarity of a previous segment. Each segment 13a–13n floats with respect to the voltage applied thereto and is independent of an adjacent segment insofar as the net voltage applied thereacross, however, it is dependent upon the polarity of the previous segment for a reference (in the case of segment 13a its reference is fixed at terminal 20a to the negative or ground side 41 (−) of bus 41).

By sharing common terminals and by the logic applied herein, the present invention reduces the number of connections for the control of multiple segments of the heating element 13 to n+1 connections wherein n is the number of segments.

By providing reversible polarity control as described herein each segment will be coupled to the bus 41 in one of four modes. For power (+) to (−) or (−) to (+) and for no power (+) to (+) or (−) to (−). Thus there is a net voltage applied for (on) or zero net voltage for (off).

The detectors Da–Dn may be differential amplifiers which respond to the voltage across the corresponding segments 13a–13n to produce an output corresponding to the resistance of the segment. The relay Ra–Rn may be of a conventional type appropriately wired to respond to the magnitude of the voltage output of the detectors Da–Dn or may be electronic transistor switches controlled by exclusive OR logic as described in the D. Johnson disclosure.

The present invention is useful for other applications requiring a heated cutting edge, notwithstanding the main thrust of the disclosure for a surgical instrument. For example, the invention could be used to cut thermoplastic material with simultaneous sealing of the cut edges.

While there has been provided, what at present is considered to be the preferred embodiment of the present invention, it will be obvious to those skilled in the art, that various changes and modifications may be made therein without departing from the invention, and it is intended in the appended claims to cover all such changes and modifications that fall within the true spirit and scope of the invention.

What is claimed is:

1. A surgical instrument for cutting tissue with electrical source powered means for providing simultaneous hemostasis, the instrument comprising: a substrate of electrically insulating material in the form of a blade having a cutting edge, having disposed thereon in the vicinity of the cutting edge an electrically heatable element of electrically conductive material exhibiting a resistance characteristic which varies as a function of the temperature, the element being divided into a plurality of independently heatable sections which form segments along said cutting edge by conducting an electrical current and directly heating the cutting edge therealong, and connection means providing electrical connection to each of said segments for independently supplying electrical power thereto, said connection means including n+1 connections for the heatable element wherein n is the number of segments forming segments of the heatable element; the connection means including a pair of conductors coupled to each adjacent segment at least one of which being a common power carrying conductor for an adjacent segment; test circuit means serially coupled to the heatable element for imposing a constant electrical input thereon to thereby produce an output response in each segment indicative of a corresponding electrical resistance, sensing means for each segment responsively connected thereto for producing a discrete output indicative of a temperature corresponding to the output response of each segment, reference means associatively coupled to each segment for establishing a reference polarity signal therefor, and switch means responsively coupled to the sensing means and reference means for coupling the source of power to each segment over the connection means in a selected polarity, such that, the selected polarity for each segment is in the same sense for an unpowered condition of the corresponding segment and in the opposite sense therefrom for a powered segment; such that, each segment may be powered and thereby heated independently.

2. The surgical cutting instrument as provided in claim 1 wherein said reference means comprises an electrical connection to one of the pair of conductors for each of said segments.

3. The surgical instrument as provided in claim 1 wherein said electrically heatable element comprises a film deposited on the cutting edge of the blade, said film exhibiting a positive or negative temperature coefficient of resistance.

4. A surgical instrument for cutting tissue with electrical source powered means for providing simultaneous hemostasis, the instrument comprising a source of electrical power having a selected voltage output and a pair of output leads coupled thereto for carrying said voltage; a substrate of electrically insulating material in the form of a blade having a cutting edge, having disposed thereon in the vicinity of the cutting edge an electrically heatable element of electrically conductive material exhibiting a resistance characteristic which varies as a function of the temperature, the element being divided into a plurality of independently heatable sections which form segments along said cutting edge by conducting an electrical current and directly heating the cutting edge therealong, and connection means providing electrical connection to each of said segments for independently supplying electrical power thereto, said connection means including n+1 connections for the heatable element wherein n is the number of segments forming segments of the heatable element; the connection means including a pair of conductors coupled to the pair of output leads and to each adjacent segment at least one of which being a common power carrying conductor for an adjacent segment, such that, the voltage supplied from the source of power across any segment is not greater than the selected voltage output; test circuit means serially coupled to the heatable element for imposing a constant electrical input thereon to thereby produce an output response in each segment indicative of a corresponding electrical resistance, sensing means for each segment responsively connected thereto for producing a discrete output indicative of a temperature corresponding to the output response of each segment, reference means associatively coupled to each segment for establishing a reference polarity signal therefor, and switch means responsively coupled to the sensing means and reference means for coupling the source of power to each segment in a selected polarity, such that, the selected polarity for each segment over the connection means is in the same sense for an unpowered condition of the corresponding segment and in the opposite sense therefrom for a powered segment; such that, each segment may be powered and thereby heated independently.

5. The surgical cutting instrument as provided in claim 4 wherein said two output leads include an electrical bus being coupled to said connection means via said switch means.

6. A control system for independently coupling a source of power to a plurality of heatable segments along a cutting edge of a surgical scalpel each being series connected one to the other, and having n+1 parallel connections thereacross at selected locations, where n is the number of heatable segments, selected ones of such n+1 connections being common power carrying conductors for adjacent heatable segments, the control system comprising: test circuit means adapted to be serially coupled to the heatable segments for imposing a constant electrical input thereon to thereby produce an output response in each heatable segment indicative of a corresponding electrical resistance, sensing means for each heatable segment adapted to be responsively coupled thereto for producing a discrete output indicative of a temperature corresponding to the output response of each heatable segment, reference means adapted to be associatively coupled to each heatable segment for establishing a reference polarity signal therefor, and switch means responsively coupled to the sensing means and reference means adapted for coupling the source of power to each heatable segment in a selected polarity, such that, the selected polarity for each segment is in the same sense for an unpowered condition of the corresponding heatable segment and in the opposite sense therefrom for a powered one.

* * * * *